United States Patent [19]
Hegenbarth et al.

[11] Patent Number: 5,364,990
[45] Date of Patent: Nov. 15, 1994

[54] AQUEOUS SUBMERSION PYROLYZATION OF FLUOROFORM

[75] Inventors: Jack Hegenbarth, Wilmington; Norman A. Street, Newark, both of Del.

[73] Assignee: W. L. Gore & Associates, Inc., Newark, Del.

[21] Appl. No.: 181,549

[22] Filed: Jan. 13, 1994

[51] Int. Cl.$^5$ ............................................. C07C 17/02
[52] U.S. Cl. .................................................... 570/159
[58] Field of Search ................................. 570/171, 159

[56] References Cited

U.S. PATENT DOCUMENTS 3,009,966  11/1961  Hauptschein .

Primary Examiner—Alan Siegel
Attorney, Agent, or Firm—Gary A. Samuels

[57] ABSTRACT

A preparation of perfluoroolefins from fluoroform is described in which the fluoroform is pyrolyzed in a flame submerged in water in which the water acts as the walls of a reaction vessel.

5 Claims, 1 Drawing Sheet

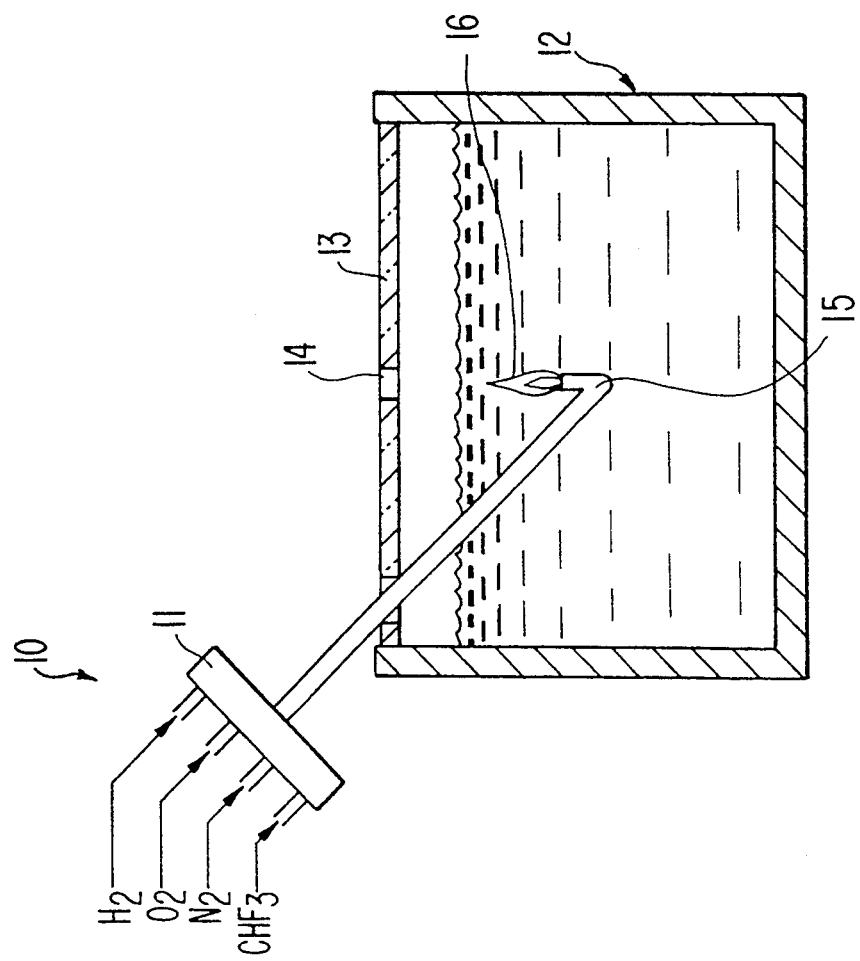

AQUEOUS SUBMERSION PYROLYZATION OF FLUOROFORM

FIELD OF THE INVENTION

This invention relates to the pyrolysis of fluoroform ($CHF_3$) to form perfluoroolefins.

BACKGROUND OF THE INVENTION

Tetrafluoroethylene (TFE) can be produced by pyrolysis of $CF_2HCl$(F-22) at about 800° C. HCl splits off and two of the remaining $CF_2$ radicals combine to form $CH_2=CH_2$. However F-22 is an ozone destroying chemical and other procedures for obtaining TFE are desirable.

In U.S. Pat. No. 3,009,966 fluoroform is converted to TFE and perfluoropropene using high temperatures, short dwell times and low pressures. However the pyrolysis temperatures are limited by the heat tolerance of the reaction vessel, which in the Examples is platinum lined nickel or simply nickel. Indeed, the patent examples use no higher temperatures than 1120° C. (Ex. 60) even though the patent states that temperatures up to 1500° C. may be used. Such a high temperature may be unrealistic since the Examples do not begin to approach that. Furthermore, the patent states at column 2, lines 1-3 that it is difficult to produce the desired products because of the extremely short contact times that must be used.

SUMMARY OF THE INVENTION

It is a purpose of this invention to provide a process for preparing perfluoroolefins especially TFE and perfluoropropene from fluoroform which overcome the deficiencies recited above.

The deficiencies may be overcome by carrying out the pyrolyzation in a flame envelope submerged in water, said flame being at a temperature of between about 1000° C. and 3000° C. and said flame being submerged in water such that the water pressure at the flame point is between about one and thirty inches of water. The surrounding water acts as a reaction vessel.

BRIEF DESCRIPTION OF THE DRAWING

The drawing is a side view, cutaway, of a vessel useful in the process of the invention.

DESCRIPTION OF THE INVENTION

In this invention equipment can be used consisting of a torch similar to a regular oxygen/hydrogen torch, modified so that gaseous nitrogen and gases such as fluoroform can also be fed. Each gas stream is supplied by storage cylinders of the conventional type equipped with conventional pressure reducers, related pressure indicators and also flowmeters.

Referring to the drawing, at the torch supply end 10, all four gas hoses are connected into an enlarged mixing header 11 by the addition of the nitrogen and fluoroform gas supplies. This means bringing two additional, separate connections to the standard system of hydrogen and oxygen mixing. The assembly follows standard practice in which the remainder of the torch is isolated by a small flame arrestor. For convenience, the pipe between the flame arrestor and the nozzle 15 can be extended and bent into an acute 45° angle so as to permit the flame to burn in an upward direction when it is immersed under water.

The water tank 12 is typically five gallon size, it will have a very light transparent, loose cover 13 with a hole 14 for gas venting. This hole is sized by experience with the particular torch employed, in order to vent products in a controlled way without lifting the light transparent cover (which is then in place for explosion release purposes). The gas space below the cover will have automatic gas sampling and an oxygen detector (not shown). This space is also fitted with a UV detector for indication that the flame has gone out. This detector connects to the fail-safe valves for automatic shut down at the cylinders. There is also a temperature indicator in the gas space as another indicator of flame out. The water space is fitted with a pH meter, and a temperature indicator for controlling the supply of water for cooling, and an overflow drain.

In operation, a flame 16 is established in air by igniting the hydrogen supply to the torch nozzle. Oxygen is then turned on and the two gases adjusted to achieve a typical stable oxy-hydrogen flame. This flame is not very luminous so that operation in a darkened area is helpful. Balanced combustion is recognized by the conventional aspect of the flame, whereby a small cone of unburned gas is luminous adjacent to the nozzle.

For subsequent repeatability, the length of the total flame envelope, from the nozzle to the envelope tip together with a description of the colors and pattern of the flame envelope and the cone are all measured and recorded. The objective is to aim for repeating this flame condition in order to optimize subsequent fluorocarbon conversion.

The established, standarized oxy-hydrogen flame is then immersed in the water in the container. Because of the 45° nozzle, the flame is then vertical but if the nozzle goes too deep for the pressure conditions, then the flame will go out. To rectify this problem, a series of different, smaller nozzles with shorter flame lengths are necessary in order to obtain a flame which is completely immersed and burning in a stable manner even though it is under water.

With the flame burning steadily underwater, nitrogen is slowly introduced at an increasing, controlled rate until the flame goes out. The flowrate of the nitrogen at this point, then becomes the basis for continued experimental operation and is called the "flame out rate."

Once again the flame is re-established underwater, but this time nitrogen flow is limited to 80% of flame out rate. This condition is used for a sufficient length of time that the oxygen detector shows that the gas in the space above the water is less than 0.5% oxygen. An inert blanket is thus established over the water and under the lightweight cover.

With the nitrogen at the steady 80% rate, the fluoroform is now added to the flame as the raw material for conversion, at a rate of 1% of the "flame out rate" of the nitrogen. Sampling of the gas space commences almost immediately since this is a process with very small reactor capacity. The flow rate of the fluoroform is increased in 1% steps subsequent to extraction of each satisfactory sample. This increase continues until the flame goes out.

In this way the characteristics of the particular nozzle and flame system (which acts as a complete reactor) are determined. This capability continues with the following steps.

Again the flame is established underwater but now, with steady, similar conditions, nitrogen is fed at a rate of 60% of the flame out rate. Once again fluoroform is fed as raw material, starting at 1% of flame out rate and again increasing this flow in steps interspersed with satisfactory gas sampling. The increases continue until once again the flame is extinguished. Consequently a second set of data steps is obtained for fluoroform conversion this particular nozzle and flame condition.

By continuing the method of stepwise decreasing nitrogen flow, associated with stepwise increases of the fluoroform feed stock, an extensive data set is obtained, and indicates the conditions such as diluent ratio which are optimum for the chosen nozzle and flame with respect to the desired end product such as tetrafluoroethylene.

Once an acceptable optimum yield is obtained and the choice is made not only between different burner nozzles but also with respect to safe operation, a collecting cover is placed on the apparatus. The collecting cover is fitted with an explosion disk and an adjacent piping nozzle for product discharge via a spray trap to subsequent refining equipment. For safety reasons, the product discharge must always be at a positive pressure. The resulting gaseous products are then collected and individually isolated.

In this present invention of submerged pyrolysis the by-product hydrogen fluoride is obtained in aqueous form and is readily available for sale in this form at various concentrations or, by the addition of KOH to the water can precipitate out at potassium fluoride which is an inert solid and therefore more readily convenient as an acceptable material for waste disposal.

In this present invention, where the combustion is submerged, the container for the reaction is the water. Thus water avoids the problems mentioned up to a rate of heat generation which causes excessive localized boiling. Since it is such an inexpensive material, and can be regularly or continuously purged, it in effect makes an excellent material of reactor construction.

In the invention very short contact times are inherent in the nature of the flame envelope and are partly a function of a particular nozzle arrangement. Because the short contact times are inherent, this is one of the features which make this system of submerged reaction desirable.

It is a notable feature of this invention that not only low contact times are inherent in the process of submerged combustion, but at the same time both the presence of oxy-hydrogen combustion and the available variations in nitrogen dilution enable the partial pressure of the fluorocarbon reaction system to be reduced in a very controllable way.

It is noteworthy that in this present invention, though it is impractical to measure the volume of the heated zone, and indeed that volume will vary with the gas flow and flame envelope length, nevertheless, it is an added advantage of this new submerged processing system, that for a given set of stable conditions, the reaction zone is very precisely bounded by the water in which it is contained.

It is the inherent size and dynamics of the submerged flame configuration which fit in so advantageously with the requirements of short contact time of the fluoroform to TFE conversion process. In fact, with flowrates of the gas feeds totalling one cubic foot/minute and with a flame envelope on the order of twelve inches long by half inch diameter, calculations show roughly that total contact times are much less than 0.5 seconds although the rapidly changing chemistry inside the flame envelope coupled with the complications of gaseous expansion due to the unknown thermal profile prevent any reasonably accurate calculation of contact time at reactive temperatures from being carried out.

As previously mentioned, one of the salient advantages of the invention is that it provides a simple and economical method of obtaining high yields and conversions of tetrafluoroethylene and perfluoropropylene direct from fluoroform. To obtain optimum yields and conversions to these two materials it is preferred to employ the combination of relatively high temperatures (preferably, from 1000° to 3000° C.) preferably 1500°–3000° C., short contact time (preferably contact times of from 0.5 to 0.010 second). Relatively high temperatures are preferred in order to increase the rate of reaction (and therefore conversion per pass). Short contact times and sub-atmospheric pressures are preferred since it has been found that these conditions maximize the yield of these two products and minimize the production of other products such as per fluoroisobutylene.

Safety considerations are important in this operation since by-products can be extremely toxic, as they include the possible occurrence of PFIB. PFIB namely, perfluoroisobutylene, is one of the most toxic substances known. Similarly, there is a significant potential for explosions arising not only from TFE decomposition but also from oxygen interaction with unlit hydrogen or from oxygen reacting with TFE or from elemental carbon reacting with oxygen. It must be noted that the presence of fluorine compounds adds many hazards to the situation particularly because of potential oxy-fluorine compounds such as $COF_2$.

For safety, the cylinder supply system is physically isolated from the reaction area, so relatively long hoses are needed to connect the cylinder system to the torch. Also, power actuated fail-safe valves are required adjacent to and downstream of the pressure reducers. The fail-safe valves must close immediately if a safety problem arises.

For safety, alertness to the flame condition is essential, and this can be determined optically as stated above, or by a sudden increase in the exit gas volume, or by an alarm from an oxygen detector which samples the gas space over the water. When this happens, the oxygen supply must be shut off immediately and be quickly followed by shut off of the hydrogen supply and the $CHF_3$ supply.

With the flame burning steadily, and a steady $CHF_3$ supply, pyrolysis is indicated by a pH meter which shows an increase in acidity as HF is formed. However, reactions may go towards the undesirable manufacture of $CF_4$ and elemental carbon. For this reason the gas space and water overflow (if any) need to be carefully watched for the presence of carbon which in the event, must trigger the same urgent oxy-hydrogen shut down procedure given above.

Much of the above process is a function of the particular choice of hydrogen torch and size of the water reservoir since the oxy-hydrogen flame will heat the water and lead to water loss through evaporation. Also, water will be formed by the reaction so that the net volume of water may or may not lead to a water overflow.

We claim:

1. A process for preparing perfluoroolefins from fluoroform which comprises pyrolyzing fluoroform in a flame envelope submerged in water, said flame being at a temperature between about 1000° C. and 3000° C., and said flame being submerged at a depth such that the water pressure around the flame envelope is between about one and thirty inches of water, and collecting the perfluoroolefins produced.

2. The process of claim 1 wherein the time the fluoroform is in the flame envelope is less than 0.5 second.

3. The process of claim 1 or 2 wherein the temperature is between 1500° C. and 2500° C.

4. The process of claim 1 or 2 wherein the flame is produced by a mixture of oxygen and hydrogen.

5. The process of claim 1, 2, 3 or 4 wherein the perfluoroolefin collected is tetrafluoroethylene.

* * * * *